United States Patent [19]

Hampden-Smith et al.

[11] Patent Number: 5,308,601
[45] Date of Patent: May 3, 1994

[54] FORMATION OF CRYSTALLINE METAL OXIDES AT LOW TEMPERATURES

[75] Inventors: Mark Hampden-Smith; Clive Chandler, both of Albuquerque, N. Mex.

[73] Assignee: University of New Mexico, Albuquerque, N. Mex.

[21] Appl. No.: 947,238

[22] Filed: Sep. 18, 1992

[51] Int. Cl.$^5$ .............................. C01F 1/00
[52] U.S. Cl. .................... 423/593; 428/598; 501/134
[58] Field of Search ........... 423/593; 428/598; 501/134

[56] References Cited

U.S. PATENT DOCUMENTS 4,968,498 11/1990 Wautier et al. ............... 423/593
5,122,360 6/1992 Harris et al. ................. 423/598
5,196,388 3/1993 Shyu .......................... 423/593

*Primary Examiner*—Mark L. Bell
*Assistant Examiner*—Willie J. Thompson
*Attorney, Agent, or Firm*—Albert Sopp; Robert E. Becker

[57] ABSTRACT

Metal oxides are formed at low temperatures by the process of providing a class of divalent metal hydroxycarboxylates designed to react with metal alkoxide compounds such as $B(OR')_4$, where $B=$Ti, Zr, Sn and $R'=$an alkyl group with the elimination of two equivalents of alcohol to form species with integral or non-integral stoichiometry. The reaction produces an intermediate compound which after thermolysis at 350° C. in $O_2$, results in formation of crystalline perovskite phase materials of general formula $ABO_3$, $A_xA'_{1-x}BO_3$ and $AB_xB'_{1-x}O_3$.

12 Claims, 4 Drawing Sheets

FORMATION OF CRYSTALLINE METAL OXIDES AT LOW TEMPERATURES

FIELD OF INVENTION

The present invention relates to the synthesis of metal hydroxycarboxylate compounds and their reaction with other metal alkoxide compounds resulting in formation of crystalline metal oxide materials at low temperatures.

BACKGROUND OF INVENTION

Perovskite phase mixed metal oxide ceramics are interesting materials due to changes in their physical properties on application of an external electrical stimulus. These properties include ferroelectric, pyroelectric, piezoelectric and dielectric behavior and have lead to numerous applications in electro-mechanic transducers, light modulation, charge storage, non-volatile memory applications and infra-red detection. (West, A. R., in "*Solid State Chemistry and Its Applications*", John Wiley and Sons, 1989. Meyers, E. R.; Kingon, A. I. eds, "*Ferroelectric Thin Films*", Materials Research Society: Pittsburgh, Pa., 1990, Vol 200. Bhalla, A. S.; Nair, K. M., Eds, "*Ceramic Transactions: Ferroelectric Films*", volume 25, The American Ceramic Society, Westerville, Ohio, 1992). Since these physical properties generall arise from the crystal chemistry of these materials, the formation of pure, stoichiometric, homogeneous, crystalline metal oxide films with controlled crystalline size is crucial. An additional problem that is commonly encountered in the formation of these materials is crystallization of the pyrochlore phase which does not exhibit the properties described above.

The different physcial properties related to the phase transitions are sensitive to the chemical composition, the purity, the number of surface and bulk defects, the grain size and the sintering conditions. The need to control these parameters is critical for the quality control of the devices produced from these materials. For example, the loss of Pb from lead titanate precursors during thermal processing is common due to the high volatility of PbO. This can be detrimental as any deviation from the correct stoichiometry will introduce $TiO_2$ as an impurity which will deteriorate the ferroelectric properties of the product.

The physical properties of these materials are often tailored through formation of non-integral stoichiometry phases. The reason for producing these materials is to tailor the properties for the particular application. For example, $BaTiO_3$ is not useful in its pure form because the high permeativity values are limited to a narrow temperature range near the Curie point at 130° C. which is outside the temperature range for electronic applications. The goal of doping $BaTiO_3$ is to lower the $T_c$ to room temperature and to broaden the temperature range over which the permeativity is high. To achieve this, partial substitution of Ca for Ba and Zr or Sn for Ti is used to give formulations of the type $Ba_{1-x}Ca_xTi_{1-x}Zr_xO_3$. By utilizing these substitutions the phase transitions which exist in pure $BaTiO_3$ can be moved into a narrow band around room temperature to give a high permeativity under these conditions.

For the successful integration of these ceramics into silicon device technology, the problems of high crystallization temperatures (>400° C.) and kinetically slow crystallization must be overcome. Low crystallization temperatures are required to prevent the degradation of the underlying materials (especially aluminum) in the device structure. To achieve this goal a great deal of research has been carried out to prepare crystalline materials at low temperatures via thermal decomposition of metal-organic precursors. This route has the advantage that thin films can be spin-coated onto the silicon wafer and fired to give the crystalline ceramic film. However, no general process for the formation of metal oxides at low temperatures (<400° C.) has been identified.

In the past, a variety of methods for the preparation of these materials has been explored. The industrial routes to $BaTiO_3$ powder involve the thermal reaction (800°–1100° C.) between $BaCO_3$ and $TiO_2$ or the thermal decomposition of $BaTiO(C_2O_4)_2.4H_2O$. Hydrothermal synthesis of $BaTiO_3$ powder has been achieved at much lower temperatures (150°–200° C.) by reaction between barium and titanium hydroxides (Vivekanandan, R.; Philip, S.; Kutty, T. R.; *Mater. Res. Bull.*, 1986, 22, 99.) in strongly alkaline (pH>12) solutions in an autoclave at >5 MPa or from barium titanium acetate gels (Hennings, D.; Rosenstien, G; Schreinemacher, H.; *J. Europ Ceram. Soc.*, 1991, 8, 107). However, the materials produced by this method exhibit some anomalous behavior thought to be derived from the incorporation of water and the presence of hydroxyl groups in the crystal lattice (Hennings, D.; Schreinemacher, H.; *J. Europ Ceram. Soc.*, 1992, 9, 41.). Liquid phase chemical approaches to perovskite phase materials through metal-organic precursors have been extensively studied (Meyers, E. R.; Kingon, A. I. eds, "*Ferroelectric Thin Films*", Materials Research Society: Pittsburgh, Pa, 1990, Vol 200. Bhalla, A. S.; Nair, K. M., Eds, "*Ceramic Transactions: Ferroelectric Films*", volume 25, The American Ceramic Society, Westerville, Ohio, 1992.) and generally involve the reaction between metal alkoxides and metal carboxylates (Brinker, C. J.; Scherer, G. W. *Sol-Gel Science, The Physics and Chemistry of Sol-Gel Processing*, Academic Press, 1990. see e.g. "*Better Ceramics Through Chemistry II, III and IV*", Brinker, C. J.; Clark D. E.; Ulrich, Eds.) followed by hydrolysis and thermally-induced condensation/crystallization in the temperature range 500°–700° C. In addition, complicated and extended annealing schedules are often necessary to ensure complete crystallization of the correct perovskite phase. In some cases, annealing in the presence of an excess of lead vapor is necessary to prevent crystallization of the pyrochlore phase and/or loss of lead and crystallization of $TiO_2$. Very few examples of the crystallization of perovskite phase materials at lower temperatures (<400° C.) exist, including $BaTiO_3$ (50° C., 12 hr. Mazdiyasni, K. S.; Dolloff, R. T.; Smith II, J. S., *J. Am. Cer. Soc.*, 1969, 52, 523, and 100° C., unspecified time, Larbot, A.; Garcia, F.; Guizard, C., Eur. J. Solid State Inorg. Chem., 1989, 26, 327, and $PbTiO_3$, (375° C., 10 hr.) Schwartz, R. W.; Payne, D. A.; *Mater. Res. Soc. Proc.*, 1988, vol. 121, 199.). These processes are specific to these systems and cannot be extended to the formation of other metal oxide materials. In addition extended heating times were necessary to form crystalline material.

Accordingly, it is desirable to access this class of integral and non-integral stoichiometry perovskite phase metal oxide compounds by a generic method that overcomes the disadvantages of the prior art compositions and enables the formation of crystalline materials at low temperatures.

SUMMARY OF INVENTION

This invention provides a method to prepare crystalline perovskite phase mixed metal oxide compounds at low temperatures. This method relies on the preparation, for each metal, of a metal hydroxycarboxylate compound designed to react with a metal alkoxide compound to produce an intermediate compound in which the alcohol is eliminated, the intermediate being a species with controlled metal atom stoichiometry. The intermediate can then be thermally decomposed at 350° C. or below under an oxygen atmosphere to form a corresponding crystalline metal oxides. Furthermore, through controlled mixing of the individual intermediates, in accordance with the invention, the formation of non-integral stoichiometry mixed metal oxides is possible. The invention provides a process for the formation of integral stoichiometry mixed metal oxides of general empirical formula $ABO_3$, where A=Ca, Sr, Ba and Pb and B=Ti, Zr and Sn. The invention also provides a process for the formation of non-integral stoichiometry mixed metal oxides of general empirical formula $AB_{1-x}B'_xO_3$ and $A_xA'_{1-x}BO_3$ where either the A cation or the B cation stoichiometry is non-integral. In the case of non-integral stoichiometry materials, A does not equal A' and B does not equal B'. These examples include $PbZr_{0.52}Ti_{0.48}O_3$ and $Ba_{0.6}Sr_{0.4}TiO_3$

DETAILED DESRIPTION OF INVENTION

The preparation of the desired metal oxides in accordance with the invention begins with the provision of a class of divalent metal α-hydroxycarboxylates of general empirical formula $A(O_2CCR_2OH)_2$ where A=Pb, Ca, Sr, Ba and R=an alkyl group, which have been prepared according to the equation below.

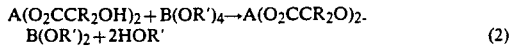

$$A(CO_3) + 2HO_2CCR_2OH \xrightarrow{H_2O} A(O_2CCR_2OH)_2 + H_2O + > CO_2 \quad (1)$$

The details of preparation of two general examples of this class of compound are described in Examples 1a–d and 2a–d. These species are designed to react with metal alkoxide compounds such as $B(OR')_4$, where B'=Ti, Zr, Sn and R'=an alkyl group with the elimination of two equivalents of alcohol to form species with a fixed A:B. stoichiometry of 1:1 according to equation 2.

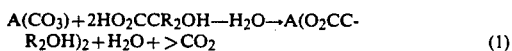

$$A(O_2CCR_2OH)_2 + B(OR')_4 \rightarrow A(O_2CCR_2O)_2\cdot B(OR')_2 + 2HOR' \quad (2)$$

When the reactions of equation 2 (R=H) are carried out in either the parent alcohol (R'OH) or with pyridine sas solvent, a white precipitate is formed. After the volatile components have been removed under vacuum, this white solid can be converted to the corresponding perovskite phase material by heating to 350° C. under an oxygen atmosphere for 30 min. in an enclosed glass reaction tube fitted with a bubbler in a tube furnace.

When the reactions of equation 2 where R=Me are carried out, the solubility of the reaction products in pyridine and dimethylformamide increased markedly to give homogeneous clear solutions. Spectroscopic data showed that the liberated alcohol was coordinated to the complex and pyridine was present, consistent with the empirical formula $A(O_2CCR_2O)_2B(OR')_2\cdot 2HOR'\cdot xC_5H_5N$. Furthermore, addition of an excess of water to these rapidly stirred solutions often resulted in initial precipitation followed by rapid re-dissolution to form transparent homogeneous solutions. This system has the advantage over the previous system that the intermediates are soluble and thus can be used for dipcoating or spin-coating these materials onto silicon substrates for the formation of crystalline metal oxide films at non-destructive low temperatures.

Figure 1:
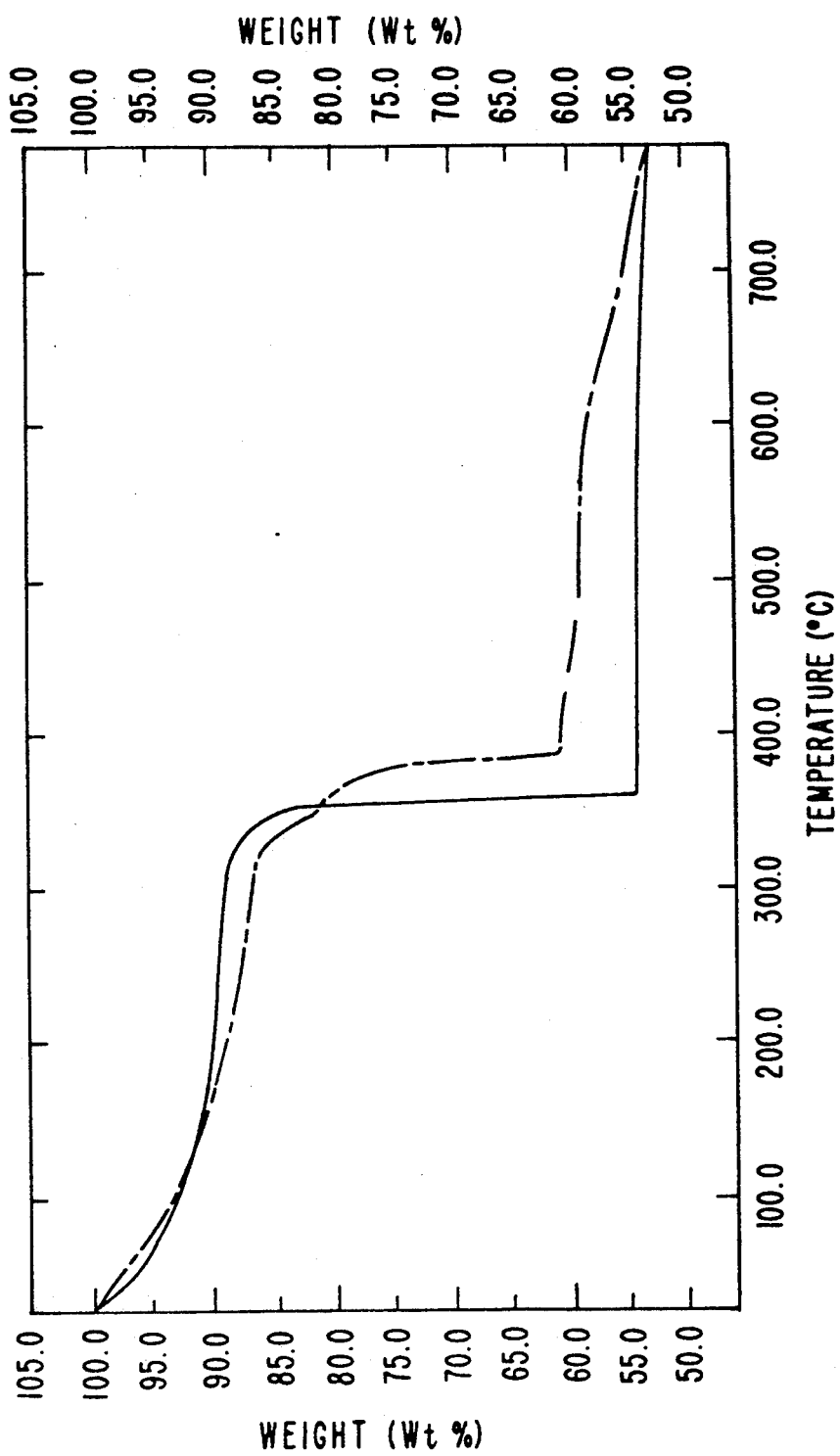
FIG. 1: Is a graph showing a plot of weight loss versus temperature for the thermal decomposition of the products of the reaction of barium dimethylglycolate with titanium isopropoxide under air and oxygen atmospheres.

When the volatile components are evaporated from these solutions in vacuo, white or pale yellow solids are formed. Elemental analyses were consistent with the empirical formula $A(O_2CCR_2O)_2B(OH)_2\cdot x(H_2O)\cdot x(C_5H_5N)$. $^1H$ and $^{13}C$ NMR data confirm that the alkoxide and alcohol ligands are removed, but the glycolate ligands are still present. Thermogravimetric analysis of these solids carried out in air and in oxygen revealed that the weight loss is always complete at lower temperatures in an oxygen atmosphere. In $O_2$, weight loss was complete after heating for about 30 min at approximately 350° C. and was consistent with formation of the corresponding metal oxide, $ABO_3$. In air, initial weight loss occurred at similar temperatures, but additional weight loss was often observed at higher temperature typically between 600° and 700° C. This higher temperature weight loss corresponded to the loss of $CO_2$ and is presumed to be derived from the formation of metal carbonates probably derived from atmospheric $CO_2$, see FIG. 1. If the unhydrolyzed material, $A(O_2CCR_2O)B(OR')_2$, is heated directly or hydrolysis is carried out in the solid state in air, TGA in $O_2$ shows retention of the high temperature weight loss step. Therefore, it appears that in the case of homogeneous hydrolysis in pyridine, removal of the volatile components in vacuo and subsequent thermolysis in $O_2$ are the optimum reaction conditions based on TGA data. The isolated, hydrolyzed intermediate solids are quite soluble in water and water/alcohol mixtures.

Figure 2:
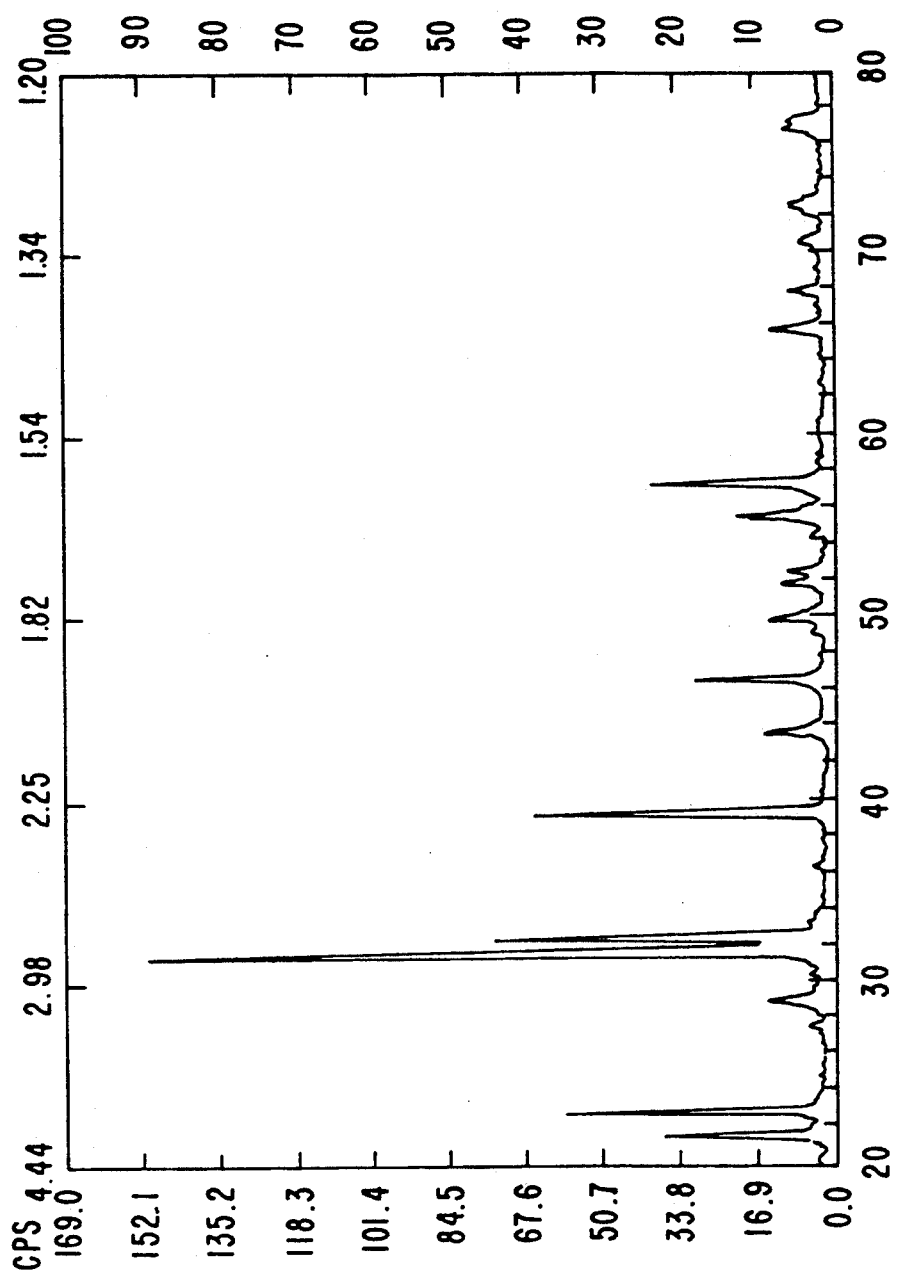
FIG. 2: Is a graph showing a X-ray diffraction pattern plot of intensity versus $2\theta$ for the thermal decomposition of the products of the reaction of lead dimethylglycolate with titanium isopropoxide showing the presence of the crystalline perovskite phase $PbTiO_3$.

Thermolysis of bulk samples of the crude mixed metal hydrolysis products after heating at 350° C. revealed that, in all cases, crystalline phases had been formed. As shown in Example 3, thermolysis of the hydrolysis product from the reaction of $Pb(O_2CCMe_2OH)_2$ and $Ti(O-i-Pr)_4$ formed crystalline perovskite phase $PbTiO_3$, as shown in FIG. 2. The sharp diffraction peaks indicate the presence of large (>1,000 Å) crystallites. All other representative species examined exhibited large crystallite sizes except $PbZrO_3$ which on heating even to 400° C. for 0.5 hr exhibited broad diffraction maxima corresponding to a crystallite size of ~30 nm.

According to the invention, the formation of non-integral stoichiometric materials via reactions between mixtures of stoichiometric precursors occur by reactions according to the general equations 3 and 4 below. In the case of non-integral stoichiometry materials, A does not equal A' and B does not equal B'.

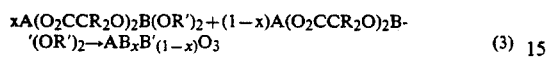

$$xA(O_2CCR_2O)_2B(OR')_2 + (1-x)A(O_2CCR_2O)_2B'(OR')_2 \rightarrow AB_xB'_{(1-x)}O_3 \quad (3)$$

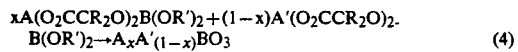

$$xA(O_2CCR_2O)_2B(OR')_2 + (1-x)A'(O_2CCR_2O)_2B(OR')_2 \rightarrow A_xA'_{(1-x)}BO_3 \quad (4)$$

Figure 3:
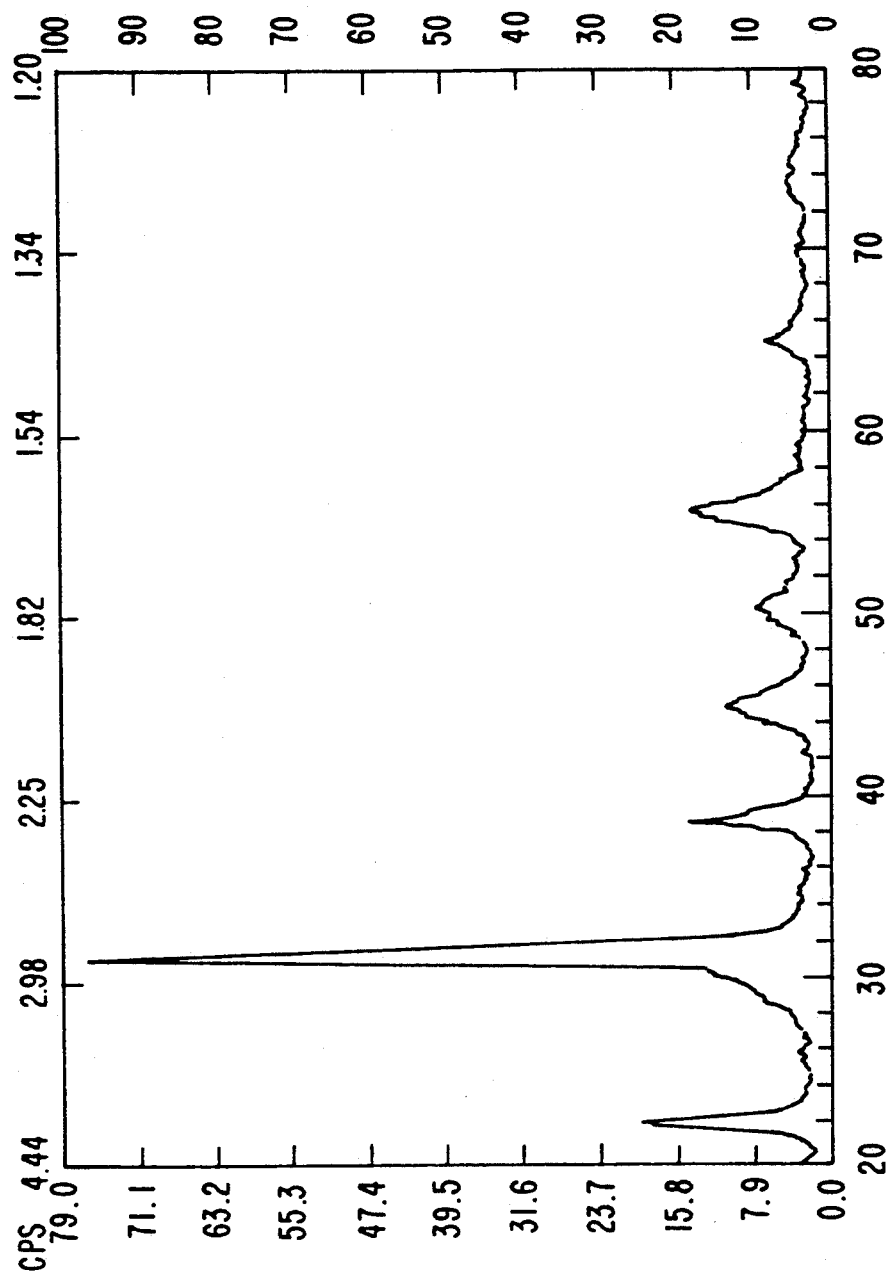
FIG. 3: Is a graph showing a X-ray diffraction pattern plot of intensity versus $2\theta$ for the thermal decomposition of the products of the reaction of lead dimethylglycolate with titanium isopropoxide and zirconium isopropoxide in the ratio 0.48:0.52 showing the presence of the crystalline perovskite phase $PbZr_{0.52}Ti_{0.48}O_3$.
Figure 4:
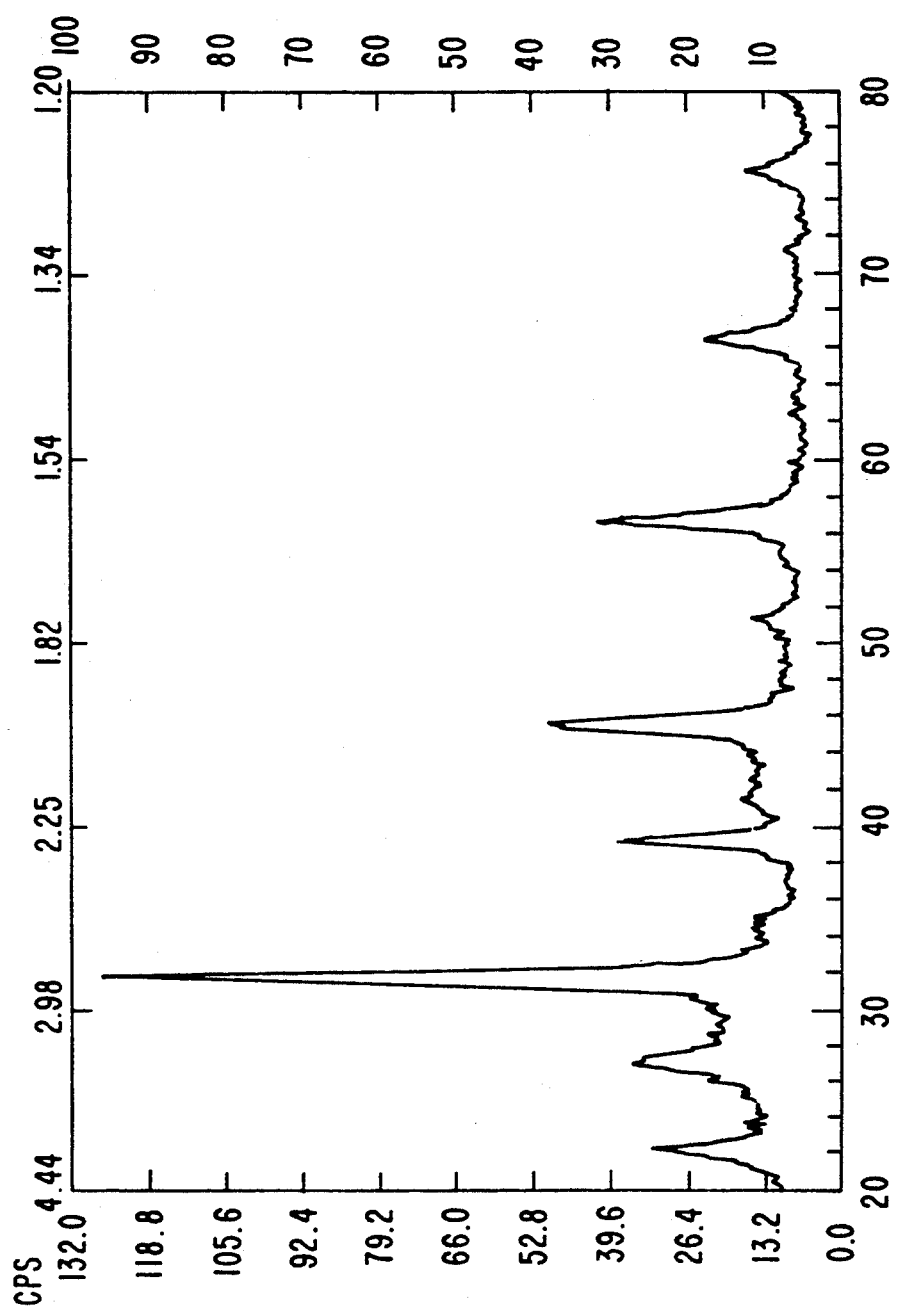
FIG. 4: Is a graph showing a X-ray diffraction pattern plot of intensity versus $2\theta$ for the thermal decomposition of the products of the reaction of barium dimethylglycolate and strontium dimethylglycolate in the ratio 0.6:0.4 with titanium isopropoxide showing the presence of the crystalline perovskite phase $Ba_{0.6}Sr_{0.4}TiO_3$

Examples of the system $AB_{1-x}B'_xO_3$ and $A_{1-x}A'_xBO_3$ are presented in Examples 4 and 5, respectively. Pyridine solutions of the hydrolysis products derived from the reactions between $Pb(O_2CCMe_2OH)_2$ and $Ti(O-i-Pr)_4$, and between $Pb(O_2CCMe_2OH)_2$ and $Zr(O-i-Pr)_4$ were mixed in the mole ratio 0.48:0.52, respectively. This ratio was chosen because it should be possible to distinguish the formation of a mixture of phases (i.e. $PbTiO_3$ and $PbZrO_3$) from the formation of the known crystalline single phase product $PbZr_{0.52}Ti_{0.48}O_3$ by X-ray powder diffraction. After mixing, the homogeneous transparent solution was stirred for 5 min., the volatile components were removed in vacuo and the deep orange solid heated to 350° C. in $O_2$ for 30 min. The X-ray powder diffraction data for the yellow solid obtained under these conditions is shown in FIG. 3. This diffraction pattern reveals only the presence of crystalline perovskite phase $PbZr_{0.52}Ti_{0.48}O_3$. A similar strategy using a mixture of Sr and Ba precursors gave $Ba_{0.6}Sr_{0.4}TiO_3$ as the only crystalline phase as shown in FIG. 4.

EXAMPLES

Example 1

Preparation of metal glycolate precursors, $A(O_2C(CH_2)OH)_2$, A = Ca, Sr, Ba and Pb

Example 1a

Preparation of $Pb(O_2CCH_2OH)_2$ $PbCO_3$ (0.02 mol) was suspended in water (20 ml) and Hydroxyacetic (0.04 mol) acid was added. The mixture effervesced and some undissolved material remained so the solution was refluxed until all of the material was dissolved. Heating was discontinued and the solution cooled overnight. Clear colorless crystals were obtained which were found to be analytically pure.

Example 1b

Preparation of $Ba(O_2CCH_2OH)_2$

The barium compound was prepared by the same method as in 1a using $BaCO_3$ as starting material. $Ba(O_2C(CH_2)OH)_2$ could not be crystallized from water but formed a glassy material which was dried at 110° C. overnight.

Example 1c

Preparation of $Sr(O_2CCH_2OH)_2$

The strontium compound was prepared by the same method as in 1a using $SrCO_3$ as starting material. $Sr(O_2C(CH_2)OH)_2$ was precipitated from water by the addition of isopropanol.

Example 1d

Preparation of $Ca(O_2CCH_2OH)_2$ $CaH_2$ (0.023 mol) was dissolved in super dry Ethanol 50 mL. 2-Hydroxyacetic acid (0.048 mol) was added and immediately dissolved. The product was obtained by cooling the solution at −6° C. overnight and collecting the precipitate.

Example 2

Preparation of metal dimethyl glycolate precursors, $A(O_2C(CMe_2)OH)_2$, A = Ca, Sr, Ba, and Pb

Example 2a

Preparation of $Pb(O_2C(CMe_2)OH)_2$ $PbCO_3$ (0.038 mol) was suspended in water (50 ml) and Hydroxyiso-butyric acid (0.076 mol) was added. The mixture effervesced and some undissolved material remained so the solution was refluxed until all of the material was dissolved. Heating was discontinued and the solution filtered then reduced to dryness. The crude material was recrystallized from 180% proof ethanol. Yield 95%

Example 2b

Preparation of $Sr(O_2C(CMe_2)OH_2$

The strontium compound was prepared by the same method as that described in Example 2a using $SrCO_3$ as starting material.

Example 2c

Preparation of $Ba(O_2C(CMe_2)OH)_2$

The barium compound was prepared by the same method as that described in Example 2a using $BaCO_3$ as starting material. Barium was precipitated from water by the addition of iso-propanol.

Example 2d

Preparation of $Ca(O_2C(CMe_2)OH)_2$ $CaH_2$ (0.004 mol) was dissolved in super dry Ethanol 50 ml. 2-Hydroxyiso-butyric acid (0.08 mol) was added and immediately dissolved. The product was obtained by cooling the solution at −6° C. overnight and collecting the precipitate.

Example 3

Preparation of Crystalline Perovskite Phase $ABO_3$ Materials where A = Ca, Sr, Ba and Pb; B = Ti, Zr, Sn A(Hydroxycarboxylate)$_2$ (0.014 mol) was dissolved in pyridine (20 mL). $B(OR)_4$ (0.014 mol) was also dissolved in pyridine (20 mL) and the two solutions mixed. The resulting solution slowly turned cloudy and deposited a precipitate. Water (2 ml) was added and the precipitate dissolved. The precursor was obtained by removing the pyridine under vacuum leaving a yellow solid. The yellow solid was placed in a glass crucible inside a furnace and heated to 350° C. for 30 min under an oxygen atmosphere. In every case the perovskite phase mixed metal oxides were formed.

Example 4

Preparation of $A_xA'_{1-x}BO_3$ Precursor

Example 4a

Method 1

A(Hydroxycarboxylate)$_2$ (7 mmol) and A'(Hydroxycarboxylate)$_2$ (7 mmol) were mixed as powders then dissolved in pyridine (20 ml). B(OR)$_4$ (0.014 mol) was also dissolved in pyridine (20 ml) and the two solutions mixed. The resulting solution slowly turned cloudy and deposited a precipitate. Water (2 ml) was added and the precipitate dissolved. The precursor was obtained by removing the pyridine leaving a yellow solid. The yellow solid was placed in a glass crucible inside a furnace and heated to 350° C. for 30 min under an oxygen atmosphere. The perovskite phase mixed metal oxides were formed.

Example 4b

Method 2

Two different solutions were prepared; Solution A: A(Hydroxycarboxylate)$_2$ (0.014 mol) was dissolved in pyridine (20 ml). B(OR)$_4$ (0.014 mol) was also dissolved in pyridine (20 ml) and the two solutions mixed. The resulting solution slowly turned cloudy and deposited a precipitate. Water (2 ml) was added and the precipitate dissolved. Solution B A'(Hydroxycarboxylate)$_2$ (0.014 mol) was dissolved in pyridine (20 ml). B(OR)$_4$ (0.014 mol) was also dissolved in pyridine (20 ml) and the two solutions mixed. The resulting solution slowly turned cloudy and deposited a precipitate. Water (2 ml) was added and the precipitate dissolved. The two hydrolyzed solutions were then mixed and stirred for an hour and the solvent was removed under vacuum. The yellow solid was placed in a glass crucible inside a furnace and heated to 350° C. for 30 min under an oxygen atmosphere. The perovskite phase mixed metal oxides were formed. By these two methods we prepared Ba$_{0.6}$Sr$_{0.4}$TiO$_3$ and Ca$_{0.4}$TiO$_3$.

Example 5

Preparation of AB$_x$B'$_{1-x}$O$_3$ precursor

Example 5a

Method 1

A(Hydroxycarboxylate)$_2$ (0.014 mol) was dissolved in pyridine (20 ml). B(OR)$_4$ (7 mmol) and B'(OR)$_4$ (7 mmol) were mixed as solids then also dissolved in pyridine (20 ml) and the two solutions mixed. The resulting solution slowly turned cloudy and deposited a precipitate. Water (2 ml) was added and the precipitate dissolved. The precursor was obtained by removing the pyridine leaving a yellow solid. The yellow solid was placed in a glass crucible inside a furnace and heated to 350° C. for 30 min under an oxygen atmosphere. The perovskite phase mixed metal oxides were formed.

Example 5a

Method 2

Two solutions were prepared; Solution A.: A(Hydroxycarboxylate)$_2$ (0.014 mol) was dissolved in pyridine (20 ml). B(OR)$_4$ (0.014 mol) was also dissolved in pyridine (20 ml) and the two solutions mixed. The resulting solution slowly turned cloudy and deposited a precipitate. Water (2 ml) was added and the precipitate dissolved. Solution B, A(Hydroxycarboxylate)$_2$ (0.014 mol) was dissolved in pyridine (20 ml). B'(OR)$_4$ (0.014 mol) was also dissolved in pyridine (20 ml) and the two solutions mixed. The resulting solution slowly turned cloudy and deposited a precipitate. Water (2 ml) was added and the precipitate dissolved. The two hydrolyzed solutions were then mixed and stirred for an hour. These methods were used to prepare PbTi$_{0.48}$Zr$_{0.52}$O$_3$ and PbTi$_{0.5}$Sn$_{0.5}$O$_3$. The solid was placed in a glass crucible inside a furnace and heated to 350° C. for 30 min under an oxygen atmosphere. The perovskite phase mixed metal oxides were formed.

We claim:

1. The method of preparing crystalline mixed metal oxide compounds for deposition or other purposes at temperatures below 400 degrees centigrade comprising the steps of:
   a) preparing a metal hydroxycarboxylate compound which reacts with a metal alkoxide compound to form one or more soluble intermediate compounds devoid of alcohol, and
   b) thermally decomposing said intermediate compound at a temperature of about 350 degrees centigrade in an O$_2$ environment, resulting in the formation of a crystalline mixed metal oxide compound.

2. The method of claim 1 wherein the crystalline mixed metal compound has integral stoichiometry.

3. The method of claim 1 wherein the crystalline mixed metal compound has nonintegral stoichiometry.

4. The method of claim 1 wherein the metal in the metal hydroxycarboxylate compound is of the group consisting of Ca, Sr, Ba, and Pb.

5. The method of claim 1 wherein the metal in the metal alkoxide compound is of the group consisting of Ti, Zr, and Sn.

6. The method of claim 1 wherein the metal hydroxycarboxylate compound has the general formula A(O$_2$CCR$_2$OH)$_2$ where A=Pb, Ca, Sr, Ba and R=an alkyl group.

7. The method of claim 6 wherein the metal hydroxycarboxylate compound has been prepared according to the equation $$A(CO_3) + 2HO_2CCR_2OH - H_2O \rightarrow A(O_2CCR_2OH)_2 + H_2O + CO_2.$$

8. The method of claim 6 wherein the metal in said metal alkoxide compound has the general formula B(OR')$_4$ where B=Ti, Zr, Sn.

9. The method of forming crystalline metal oxide materials comprising the steps of:
   a) synthesizing a class of divalent metal hydroxycarboxylates of general formula A(O$_2$CCR$_2$OH)$_2$ where A=Pb, Ca, Sr, Ba and R-an alkyl group;
   b) reacting in an O$_2$ atmosphere at about 350 degrees centigrade, said hydroxycarboxylates with precursor metal alkoxide compounds of the form B(OR')$_4$ where B=Ti, Zr, Sn, and R'=an alkyl group to from crystalline metal oxide species of either integral stoichiometric phase in the form ABO$_3$ or non-integral stoichiometric phase in the form AB$_x$B$_{(1-x)}$O$_3$ or A$_x$A'$_{1-x}$BO$_3$.

10. The method of claim 9 wherein the metal alkoxide compound for the integral stoichiometric phase is in the form A(O$_2$CCR$_2$O)$_2$B(OR')$_2$.

11. The method of claim 9 wherein the precursor metal alkoxide compound for the nonintegral stoichiometric phase is in the form xA(O$_2$CCR$_2$O)$_2$B(OR')$_2$+(1-x)A(O$_2$CCR$_2$O)$_2$B'(OR)$_2$ or xA(O$_2$CCR$_2$O)$_2$B(OR')$_2$+(1-x)A' x)A'(O$_2$CCR$_2$O)$_2$B(OR)$_2$ wherein case of stoichiometry materials A does not equal A' and B does not equal B'.

12. The method of claim 9 wherein the precursor metal alkoxide compound has been hydrolyzed for the non-integral stoichiometric phase and is in the form xA(O$_2$CCR$_2$O)$_2$B(OH)$_2$+(1-x)A(O$_2$CCR$_2$O)$_2$B(OH)$_2$ +(1-x)A'(O$_2$CCR$_2$O)$_2$B(OH)$_2$ where is the case of non-integral stoichiometry materials A does not equal A' and B does not equal B'.

* * * * *